United States Patent [19]

Kleinschmidt et al.

[11] Patent Number: 4,542,740
[45] Date of Patent: Sep. 24, 1985

[54] GAS DOSING DEVICE FOR MEDICAL APPARATUS

[75] Inventors: Lothar Kleinschmidt, Krummesse; Carl F. Wallroth; Heye Harms, both of Lubeck, all of Fed. Rep. of Germany

[73] Assignee: Drägerwerk Aktiengesellschaft, Fed. Rep. of Germany

[21] Appl. No.: 513,066

[22] Filed: Jul. 12, 1983

[30] Foreign Application Priority Data

Aug. 6, 1982 [DE] Fed. Rep. of Germany ....... 3229328

[51] Int. Cl.⁴ ............................................. A61M 16/00
[52] U.S. Cl. .......................... 128/204.21; 128/205.24; 222/3; 222/55; 137/487.5
[58] Field of Search ...................... 128/204.21, 204.23, 128/204.24, 204.25, 203.12, 203.14, 204.18, 204.22, 204.26, 204.27, 204.28, 205.13, 205.14, 205.15, 205.18, 205.24, 203.25; 222/3, 55, 57; 137/487.5

[56] References Cited

U.S. PATENT DOCUMENTS 3,662,751 5/1972 Barkalow et al. ............. 128/204.25
4,186,737 2/1980 Valenta et al. ................ 128/204.24
4,461,293 7/1984 Chen ............................. 128/204.24

*Primary Examiner*—Henry J. Recla
*Attorney, Agent, or Firm*—McGlew and Tuttle

[57] ABSTRACT

A gas dosing device for medical apparatus uses electrical control signals for connecting a gas supply under pressure through a pressure reducer to an outlet which is connected to the use load for the gas. The device includes a buffer connected between the gas source and the outlet and a reversing valve connected to the buffer and to the outlet. A pressure valve connected to the buffer and to the outlet. A pressure chamber is connected to the buffer and a measuring chamber is connected to the reversing valve. A differential pressure transducer has one connection to the pressure chamber and another to the measuring chamber and thus receives a differential of the pressure between these chambers. A control is connected to the reversing valve and to the differential pressure transducer and in accordance with the pressure which it senses in that transducer it shifts the reversing valve so that it shifts the connection of the measuring transducer to the buffer to a connection of the measuring chamber to the outlet in accordance with the pressure in the pressure transducer.

4 Claims, 2 Drawing Figures

GAS DOSING DEVICE FOR MEDICAL APPARATUS

FIELD AND BACKGROUND OF THE INVENTION

This invention relates in general to devices for supplying gas under pressure particularly for medical services and in particular to a new and useful gas dosing device for medical apparatus.

The gas dosing device can be used for medical apparatus wherever electrical control signals exist. The gas flow required there should be adjustable from 0.01 to 20 l/min.

A known arrangement for the electrically controlled dosing and mixing of gases contains in each feed line of the gases upstream of the mixing point a quick-action pilot valve. The pilot valves are on-off valves whose gas passage in the open state in dependence on two existing pressure difference is known. They are electrically controlled by a regulator which contains an arithmetic unit. A pressure converter is arranged in each feed line head of the pilot valve and in the common mixed-gas line and it is connected with the regulator.

Based on the known characteristic value, the measured pressures, as well as the given values for flow and mixing ratio, the regulator controls the passage of the pilot valves in a time slot pattern from which the desired dosing and mixing is obtained (German AS 29 31 856).

By using only one gas, the arrangement could still be used as a strict dosing device. But determining the dosing would require an elaborate quick-action computer which integrates the changing gas passage within the individual pulse. The gas pulses within this dynamic process have transient effects which limit the accuracy of the volume dosing.

SUMMARY OF THE INVENTION

The invention provides a gas dosing device for medical apparatus whose gas flow can be regulated within prescribed limits, independent of the supply or inlet pressure.

According to the invention, a buffer is connected by pipe lines from a dosing unit over a pressure reducer with a gas source, whereby a pressure chamber and a measuring chamber parallel to the pressure chamber are connected over a reversing valve whose other connection is the outlet, and where the values from the differential pressure transducer are controlled by the reversing valve with a control unit.

The gas dosing device according to the invention controls the switching over of the pressure after filling the measuring chamber. The pressure, which may slightly fluctuate in the system, does not influence the gas volume and thus the dosing. The mechanical design is simple and can be effected with known elements.

In a further development of the invention, the solution permits the determination of the further dosing range of 0.01 to 20 l/min, by the juxtaposition of the dosing units, which differ as to their chambers, but are otherwise identical.

In accordance with the invention, the gas for medical use is directed from a gas source under pressure through a pressure reducer to a dosing device which includes a buffer connected to a reversing valve and through a throttle to an outlet for connection of the gas to a source of use. In accordance with the invention, a pressure chamber is connected to the buffer and a measuring chamber is connected to the reversing valve, and each of the chambers are connected to a differential pressure transducer. The control is connected to the differential pressure transducer and senses the pressure difference between the two chambers and it is connected to the reversing valve so that it switches the connection of the measuring chamber to the buffer to a connection of the measuring chamber to the outlet. The control includes a nominal value input and an indicator of the pressure in the differential pressure transducer. The gas which passes from the measuring chamber through the reversing valve is advantageously directed through a throttle to the outlet. In another embodiment a plurality of dosing devices may be employed including one for a low flow dosing unit and one for a high flow dosing unit which are connected together so as to feed either a low range flow meter or a high range flow meter which directs the gas to the outlet.

A further object of the invention is to provide a gas dosing device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
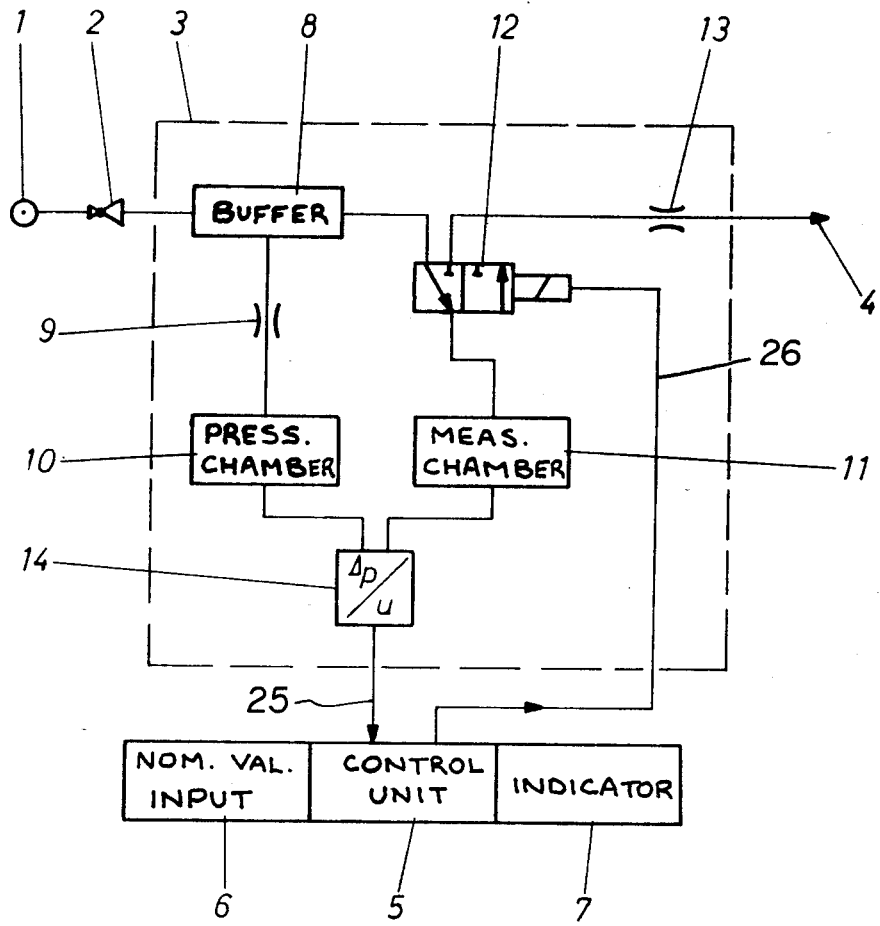
FIG. 1 is a schematic diagram of a dosing device constructed in accordance with the invention.

Referring to the drawings in particular, the invention embodied therein in FIG. 1 comprises a gas dosing device 3 for medical apparatus which uses an electrical control signal for connecting a gas supply 1 which is under pressure through a pressure reducer 2 through the dosing device 3 to an outlet 4 for connecting gas at the corrected pressure to a source of use. The dosing device comprises a buffer 8 which is connected between the gas source 1 and the outlet 4 along with a reversing valve 12 which is connected to the buffer 8 and to the outlet 4. The buffer 8 prevents the passage of abrupt pressure changes to the following structure. A pressure chamber 10 is connected to the buffer 8 and a measuring chamber 11 is connected to the reversing valve 12. A differential pressure transducer 14 has one connection to the pressure chamber 10 and another connection to the measuring chamber 11 so it receives a differential of the pressures between the chambers 10 and 11. Control means including a control unit 5 are connected through a control line 25 to the differential pressure transducer 14 and through an electrical or other suitable connection 26 to the reversing valve 12. Control means acts on the reversing valve in accordance with the pressure sensed in the transducer 14 and shifts the connection of the measuring chamber 11 from the buffer 8 to the outlet 4. Control means advantageously includes a nominal value input 6 and an indicator 7. The gas which is directed from the reversing valve to the outlet is advantageously passed through a throttle 13.

The dosing unit 3 is supplied from gas source 1 over pressure reducer 2 with gas, and gives off gas, in doses, over the outlet 4 to a load. The control unit 5 controls dosing unit 3 based on signals which it receives from dosing unit 3 and from its nominal value input 6. The adjusted values are indicated in indicator 7. In dosing unit 3, buffer 8 is connected over corresponding pipe lines to pressure reducer 2, and pressure chamber 10 is connected to buffer 8 through a throttle 9. In addition, measuring chamber 11 is connected over a reversing valve 12 in its represented neutral position with the buffer 8, and in its switched position over throttle 13 to outlet 4. The differential pressure transducer 14 is connected by gas lines with the pressure chamber 10 and also to the measuring chamber 11, and by electrical signal line 25 with the control unit 5. Reversing valve 12 is driven electrically by the control unit 5.

In operation, the gas to be dosed flows from gas source 1 through the pressure reducer 2, the buffer 8, and the reversing valve 12, into the measuring chamber 11 and fills the chamber 11 up to the operating pressure. The pressure chamber 10 has an operating pressure supplied through the operating throttle 9. With pressure equality in the pressure chamber 10 and measuring chamber 11 as determined by differential pressure transducer 14, control unit 5 switches reversing valve 12 into its switch position in which the gas from the measuring chamber 11 flows through the throttle 13 to the load and the pressure in measuring chamber 11 drops. When the resulting pressure difference from the operating pressure, determined by differential pressure transducer 14, attains a given limit value, control unit 5 switches reversing valve 12 back into its neutral position, and the above described cycle starts again.

Throttle 9 prevents the pressure in pressure chamber 10 from dropping with the filling surge of measuring chamber 11 temporarily below the operating pressure and that pressure equality is already determind at a too low pressure by pressure differential transducer 14, causing a switch.

From the known volume of the measuring chamber 11 and the known pressure difference results the amount of gas dosed with each cycle. With the values determined over nominal value input 6, control unit 5 determines the sequence of switching cycles. The gas flow results from the measuring chamber volume X of the pressure difference an x of the switching frequency. Throttle 13 stores or holds back an amount of gas given off from measuring chamber 11 in each cycle and ensures for each load a quasi-continuous flow.

Figure 2:
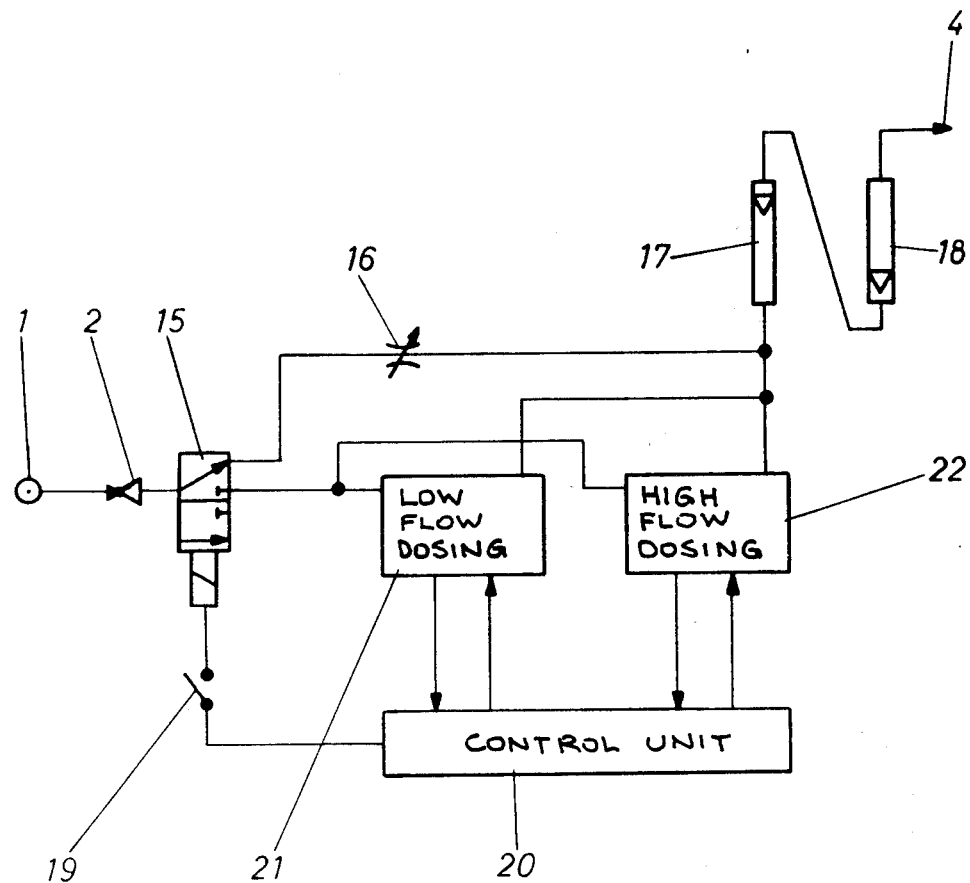
FIG. 2 is a schematic drawing showing a plurality of dosing units combined in a dosing device for medical use, constructed in accordance with the invention.

In the arrangement according to FIG. 2, a multi-way valve 15 is arranged behind gas source 1 and pressure reducer 2. In its represented neutral position, the gas flows over a manually operated adjusting valve 16 and two series connected flow meters 17, 18 of different ranges to outlet 4. Multi-way valve 15 is driven in series connection over a manual switch 19 and a control unit 20. In a failure of control unit 20, multi-way valve 15 assumes the represented neutral position, so that dosing in manual operation is always possible. By opening manual switch 19, the manual operation can be started at will at any time. With manual switch 19 closed, multi-way valve 15 connects, in its switch position, pressure reducer 2 with the input of the a dosing unit for a low flow 21 and a dosing unit for a high flow 22.

Dosing units 21, 22 correspond in their design and function to dosing unit 3, but differ in the dimensioning of the individual parts, particulaly measuring chamber 11 and throttle 13. That is, each of units 21 and 22 looks like unit 3 in FIG. 1, but has a different capacity for its chamber 11. The entire working range exceeds thus the limit of the adjustment set in an individual dosing unit. For example, each dosing unit has an adjusting possibility of 1:100. The dosing unit for a low flow 21 works then in the range 0.01 to 1 l/min, the dosing unit for a high flow 22 in the range 0.2 to 20 l/min. Control unit 20 comprises in addition a nominal value input; and an indicator for the operating stage, which can also be connected to a superordinated telecontrol system, is connected to both dosing units 21, 22 and starts one of them. Depending on the programming, the selection of operating dosing units 21 or 22 is effected in dependence on the nominal input values by control unit 20 or can be provided by external input.

The outputs of dosing units 21 and 22 are connected with the input of flow meter 17. From there the dosed gas flows over flow meters 17 and 18 to outlet 4. Flow meter 17 has a low indicating range fitting the dosing unit for a low flow 21, flow meter 18 fits the dosing unit for a high flow 22. One of the flow meters 17 or 18, which fits the respective operating dosing unit, can be read in its indicating range. Flow meters 17, 18 form for manual operation the measuring instrument for the adjustment, and in automatic operation control, in addition to the indication of control unit 20.

While specific embodiments of the invention have been shown and described in detail to illustrate the application of the principles of the invention, it will be understood that the invention may be embodied otherwise without departing from such principles.

What is claimed is:

1. A gas dosing device for medical apparatus, comprising:

a gas supply source (1);

a pressure reducer (2) having an input connected to said gas supply source, and an output;

at least one dosing unit (3) having a buffer (8) with an input connected to said pressure reducer output, a first output and a second output;

said dosing unit including a pressure chamber (10) connected to said first output of said buffer with a first throttle (9) on said first output of said buffer for throttling gas supplied from said buffer to said pressure chamber, and a reversing valve (12) having an input connected to said second output of said buffer, an output and a reversing connection for receiving and discharging gas, said reversing valve having a first position for passing gas from said buffer second output to said reversing connection, and a second position for passing gas from said reversing connection to said reversing valve output;

said dosing unit including a measuring chamber (11) connected to said reversing connection for receiving and discharging gas to and from said reversing connection, and a differential pressure transducer (14) connected to said pressure chamber and to said measuring chamber for generating a signal corresponding to a difference of pressure between said pressure chamber and said measuring chamber;

control means (5) connected to said differential pressure transducer and to said reversing valve for controlling said reversing valve to move said valve into said second position thereof when said signal from said transducer indicates an equality of pressures in said pressure chamber and said measuring chamber, and for moving said reversing valve into said first position thereof when said signal from said transducer indicates a selected difference in pressure between said pressure chamber and said measuring chamber, said control means including a control unit connected to said transducer and to said reversing valve for controlling said reversing valve, a nominal value input connected to said control unit for setting the selected pressure difference between said pressure chamber and said measuring chamber; and said dosing unit including a unit outlet (4) connected to said reversing valve outlet for supplying dosed gas.

2. A gas dosing device according to claim 1, including a second throttle (13) in said unit outlet (4).

3. A gas dosing device according to claim 2, wherein said control means includes an indicator connected to said control unit for indicating the differential in pressure between said pressure chamber and said measuring chamber.

4. A gas dosing device according to claim 1, including a second dosing unit (22) which includes all elements of said at least one dosing unit (21), said measuring chamber of said at least one dosing unit having a low capacity and a measuring chamber of said second dosing unit having a high capacity compared to said low capacity of said measuring chamber of said at least one dosing unit, a manually controllable valve (15) having an input connected to said pressure reducer (12) output, a first output and a second output, said manually controllable switch having a first position for supplying gas to said first output and a second position for supplying gas to said second output thereof, said second output connected to said input of the buffer in each of said at least one and second dosing units (21,22), said gas dosing device having a combined unit outlet connected to the unit outlet of each said at least one and second dosing units, said first output of said manually controllable switch connected to said combined unit outlet, a variable throttle valve (16) connected in said first output of said manually controllable valve (15), said control means connected to the transducer of each of said at least one and second dosing units, and to the reversing valve of each of said at least one and second dosing units for the control thereof, and a manually controlled switch connected between said control means and said manually controllable valve, said switch having an open position for moving said manually controllable valve into its first position and said switch having a closed position for moving said manually controllable valve into its second position.

* * * * *